(12) United States Patent
Pearl et al.

(10) Patent No.: US 9,958,570 B2
(45) Date of Patent: May 1, 2018

(54) ANALYSIS OF A RESERVOIR FLUID USING A MOLECULAR FACTOR COMPUTATIONAL SYSTEM

(71) Applicant: Halliburton Energy Services, Inc., Houston, TX (US)

(72) Inventors: Megan R. Pearl, Rio de Janeiro (BR); William C. Pearl, Jr., Rio de Janeiro (BR)

(73) Assignee: Halliburton Energy Services, Inc., Houston, TX (US)

(*) Notice: Subject to any disclaimer, the term of this patent is extended or adjusted under 35 U.S.C. 154(b) by 35 days.

(21) Appl. No.: 15/022,892

(22) PCT Filed: Dec. 10, 2013

(86) PCT No.: PCT/US2013/074066
§ 371 (c)(1),
(2) Date: Mar. 17, 2016

(87) PCT Pub. No.: WO2015/088493
PCT Pub. Date: Jun. 18, 2015

(65) Prior Publication Data
US 2016/0223709 A1 Aug. 4, 2016

(51) Int. Cl.
*G01V 8/12* (2006.01)
*G01N 33/22* (2006.01)
*G01J 3/42* (2006.01)
*G01J 3/457* (2006.01)
*G01N 21/31* (2006.01)
(Continued)

(52) U.S. Cl.
CPC .............. *G01V 8/12* (2013.01); *E21B 49/08* (2013.01); *G01J 3/42* (2013.01); *G01J 3/457* (2013.01); *G01N 21/31* (2013.01); *G01N 33/22* (2013.01); *G01V 9/005* (2013.01); *E21B 2049/085* (2013.01); *G01J 2003/1213* (2013.01); *G01N 21/35* (2013.01); *G01N 21/39* (2013.01); *G01N 21/85* (2013.01); *G01N 33/2823* (2013.01)

(58) Field of Classification Search
CPC ............ E21B 49/08; G01J 3/42; G01N 21/31
See application file for complete search history.

(56) References Cited

U.S. PATENT DOCUMENTS 6,649,416 B1 11/2003 Kauer et al.
7,251,032 B2 7/2007 Lodder et al.
(Continued)

FOREIGN PATENT DOCUMENTS

EP     1057118 B1    5/2003

OTHER PUBLICATIONS

Brooke, Heather, et al. "Multimode imaging in the thermal infrared for chemical contrast enhancement. Part 1: methodology." Analytical chemistry 82.20 (2010): 8412-8420.
(Continued)

*Primary Examiner* — Casey Bryant
(74) *Attorney, Agent, or Firm* — McGuireWoods LLP

(57) ABSTRACT

A method of analyzing a reservoir fluid comprising: providing an analyzer, wherein the analyzer is a molecular factor computational system; and determining at least one property of the reservoir fluid using the analyzer, wherein the step of determining comprises: causing or allowing energy to interact with the reservoir fluid; and detecting the interaction between the energy and the reservoir fluid.

10 Claims, 3 Drawing Sheets

(51) Int. Cl.
*E21B 49/08* (2006.01)
*G01V 9/00* (2006.01)
*G01J 3/12* (2006.01)
*G01N 21/35* (2014.01)
*G01N 21/39* (2006.01)
*G01N 21/85* (2006.01)
*G01N 33/28* (2006.01)

(56) References Cited

U.S. PATENT DOCUMENTS

| | | | |
|---|---|---|---|
| 7,336,356 | B2 | 2/2008 | Vannuffelen et al. |
| 7,362,422 | B2 | 4/2008 | DiFoggio |
| 7,379,180 | B2 | 5/2008 | Vannuffelen et al. |
| 7,408,645 | B2 | 8/2008 | DiFoggio |
| 7,697,141 | B2 | 4/2010 | Jones et al. |
| 7,783,458 | B2 | 8/2010 | Claps |
| 8,164,050 | B2 | 4/2012 | Ford et al. |
| 8,212,213 | B2 | 7/2012 | Myrick et al. |
| 8,237,920 | B2 | 8/2012 | Jones et al. |
| 8,283,633 | B2 | 10/2012 | Myrick et al. |
| 8,373,860 | B2 | 2/2013 | Kiesel et al. |
| 2006/0142650 | A1 | 6/2006 | Lodder et al. |
| 2006/0175547 | A1* | 8/2006 | DiFoggio ............ G01J 3/02 250/269.1 |
| 2007/0001116 | A1 | 1/2007 | Hayes |
| 2007/0215900 | A1 | 9/2007 | Maimon |
| 2008/0094624 | A1 | 4/2008 | Harsh et al. |
| 2008/0186494 | A1 | 8/2008 | Kiesel et al. |
| 2009/0250613 | A1* | 10/2009 | Myrick ............ G01J 3/42 250/339.04 |
| 2010/0201988 | A1 | 8/2010 | Kiesel et al. |
| 2011/0222062 | A1 | 9/2011 | Martini et al. |

OTHER PUBLICATIONS

Brooke, Heather, et al. "Multimode imaging in the thermal infrared for chemical contrast enhancement. Part 2: Simulation driven design." Analytical chemistry 82.20 (2010): 8421-8426.
Brooke, Heather, et al. "Multimode imaging in the thermal infrared for chemical contrast enhancement. Part 3: visualizing blood on fabrics." Analytical chemistry 82.20 (2010): 8427-8431.
International Search Report and Written Opinion dated Sep. 17, 2014; International PCT Application No. PCT/US2013/074066.
"Anisotropic Polarized Light Scatter and Molecular Factor Computing in Pharmaceutical Cleaning Validation and Biomedical Spectroscopy (Thesis);" Urbas 2007.
"Simulations-Guided Design of Process Analytical Sensor Using Molecular Factor Computing (Thesis);" Dai, 2007.
"Molecular Factor Computing for Predictive Spectroscopy;" Dai et al., 2007.

* cited by examiner

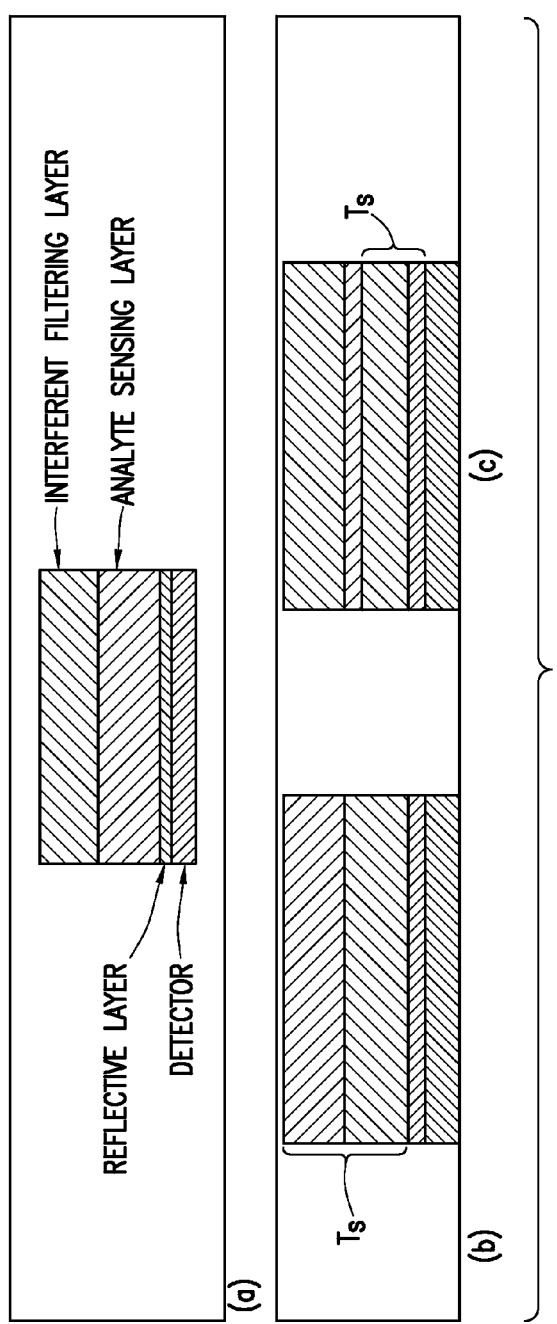
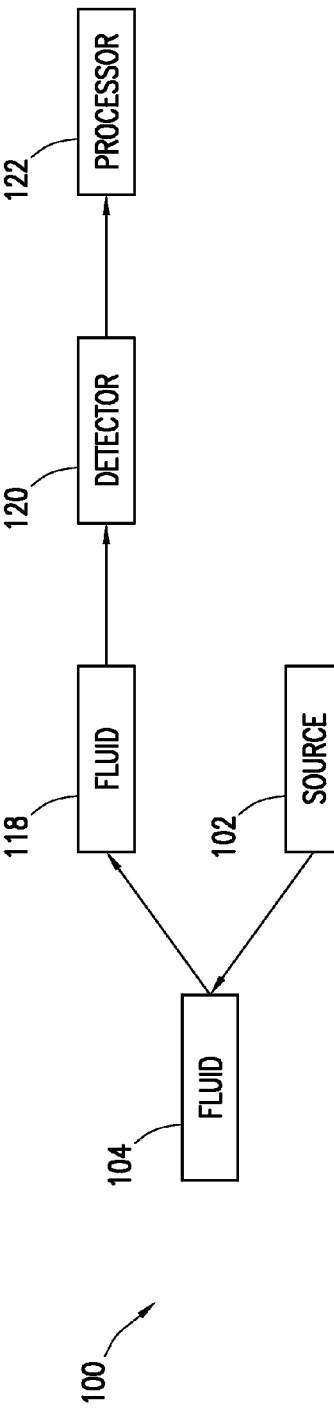
FIG. 3
FIG. 4 es or adjacent to a reservoir. The oil, gas, and/or water located in the reservoir is called a reservoir fluid. It is to be understood that a reservoir fluid originates from a reservoir underground, but can be produced from the reservoir to the surface of the land and then stored and/or transported above ground.

ANALYSIS OF A RESERVOIR FLUID USING A MOLECULAR FACTOR COMPUTATIONAL SYSTEM

TECHNICAL FIELD

This disclosure relates to optical analysis systems and methods for analyzing fluids, for example, crude petroleum. The fluids can be static or flowing, for example, flowing in a pipe, or in an oil or gas well, or being extracted from a well or from a subterranean formation, and in particular, to optical analysis systems for analyzing one or more properties of reservoir fluids.

BRIEF DESCRIPTION OF THE FIGURES

The features and advantages of certain embodiments will be more readily appreciated when considered in conjunction with the accompanying figures. The figures are not to be construed as limiting any of the preferred embodiments.

FIG. 3 is a schematic illustration of the MFC detector in which different frequency modulations are utilized.

FIG. 4 is a block diagram of an MFC system utilizing a filter according to an embodiment.

DETAILED DESCRIPTION

Figure 1:
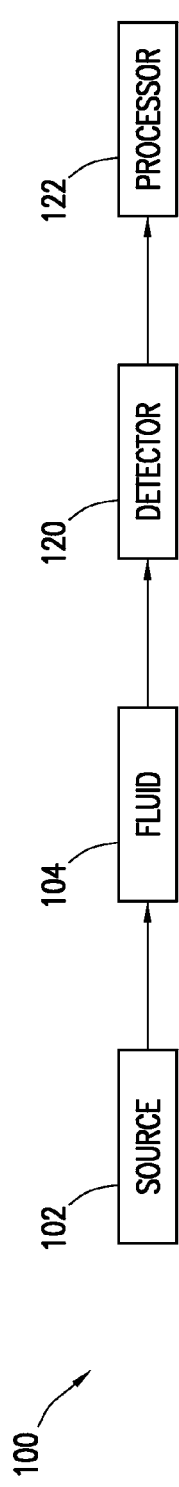
FIG. 1 is a block diagram of a molecular factor computational system according to an embodiment.

As used herein, the words "comprise," "have," "include," and all grammatical variations thereof are each intended to have an open, non-limiting meaning that does not exclude additional elements or steps.

It should be understood that, as used herein, "first," "second," "third," etc., are arbitrarily assigned and are merely intended to differentiate between two or more layers, filters, etc., as the case may be, and does not indicate any sequence. Furthermore, it is to be understood that the mere use of the term "first" does not require that there be any "second," and the mere use of the term "second" does not require that there be any "third," etc.

As used herein, a "fluid" is a substance having a continuous phase that tends to flow and to conform to the outline of its container when the substance is tested at a temperature of 71° F. (22° C.) and a pressure of one atmosphere "atm" (0.1 megapascals "MPa"). A fluid can be a liquid or gas. A fluid can have only one phase or more than one phase. In the oil and gas industry, a fluid having only one phase is commonly referred to as a single-phase fluid and a fluid having more than one phase is commonly referred to as a multi-phase fluid. A heterogeneous fluid is an example of a multi-phase fluid. A heterogeneous fluid can be: a slurry, which includes a continuous liquid phase and undissolved solid particles as the dispersed phase; an emulsion, which includes a continuous liquid phase and at least one dispersed phase of immiscible liquid droplets; a foam, which includes a continuous liquid phase and a gas as the dispersed phase; or a mist, which includes a continuous gas phase and liquid droplets as the dispersed phase.

Oil and gas hydrocarbons are naturally occurring in some subterranean formations. In the oil and gas industry, a subterranean formation containing oil or gas is referred to as a reservoir. A reservoir may be located under land or off shore. Reservoirs are typically located in the range of a few hundred feet (shallow reservoirs) to a few tens of thousands of feet (ultra-deep reservoirs). In order to produce oil or gas, a wellbore is drilled into a reservoir or adjacent to a reservoir. The oil, gas, and/or water located in the reservoir is called a reservoir fluid. It is to be understood that a reservoir fluid originates from a reservoir underground, but can be produced from the reservoir to the surface of the land and then stored and/or transported above ground.

A well can include, without limitation, an oil, gas, or water production well, or an injection well. As used herein, a "well" includes at least one wellbore. The wellbore is drilled into a subterranean formation. The subterranean formation can be a part of a reservoir or adjacent to a reservoir. A wellbore can include vertical, inclined, and horizontal portions, and it can be straight, curved, or branched. As used herein, the term "wellbore" includes any cased, and any uncased, open-hole portion of the wellbore. A near-wellbore region is the subterranean material and rock of the subterranean formation surrounding the wellbore. As used herein, a "well" also includes the near-wellbore region.

In the oil and gas industry it is often desirable to analyze a portion of a reservoir fluid because a reservoir fluid can contain one or more substances that might be detrimental to wellbore operations. For example, a wellbore fluid can contain a corrosive substance that might be harmful to wellbore equipment, such as pumping equipment or pipes. Examples of corrosive substances include, but are not limited to, high amounts of an acid gas, such as carbon dioxide gas (acid gas wells) and wells containing high amounts of a sour gas, such as hydrogen sulfide gas (sour gas wells).

Another potentially detrimental substance is an asphaltene. If asphaltenes are present in the reservoir fluid, then generally they are in solution due to being stabilized by resins. However, if the relative resin content decreases, then the asphaltenes may precipitate out of the fluid and deposit on pipe walls, thus restricting or interrupting fluid flow. It is relatively costly to remove such asphalt deposits, which may require grinding or scraping operations for removal. Other potentially detrimental substances are aromatics and naphthenates. When combined with water, aromatics and naphthenates can cause foaming of the solution, somewhat like when water is combined with soap. The foam can also restrict or interrupt fluid flow.

Another potentially detrimental substance is a gas hydrate. Generally, a substance containing between one and six carbon atoms ($C_1$ to $C_6$) is a gas at wellbore temperatures and pressures. However, during wellbore operations, depending on the temperature at the wellhead, some or all of the gas may form gas hydrates. Gas hydrates occur naturally onshore in permafrost regions, and at certain depths in the sea where water and gas combine at low temperatures and high pressures to form the hydrate. Methane ($C_1$), or natural gas, is typically the dominant gas in the hydrate structure. As gas emerges from the wellhead, water molecules from the surrounding environment form a cage-like structure around high concentrations of the gas molecules and freeze into a solid gas/water structure. If a sufficient amount of gas hydrates form, the hydrates can block or clog valves and pipes leading to the surface from the cap. As such it may be desirable to test a reservoir fluid for its gas-to-oil (GOR) ratio. This ratio, along with the temperature at the wellhead, can be useful in predicting the likelihood of gas hydrate formation.

There are several devices that can be used to analyze a fluid. Some devices are designed to be used in a laboratory setting and other devices can be used in a well or at or near the well site. Optical spectroscopy is an analytical technique that derives information about the system being evaluated by the interaction of that system with light in the ultraviolet "UV" to the infrared "IR" range. The interaction changes the properties of the light, specifically the frequency, intensity, polarization, or direction (scattering or refraction).

An example of an analyzer that can be used to analyze a fluid is a molecular factor computational (MFC) system. An MFC system is described fully in U.S. Pat. No. 8,212,213 B2, issued on Jul. 3, 2012 to Myrick, et al., which is hereby incorporated by reference in its entirety for all purposes. If there is any conflict in the usages of a word or term in this specification and one or more patents or other documents that may be incorporated herein by reference, then the definitions that are consistent with this specification control and should be adopted.

The MFC system can be used to analyze a fluid sample for a variety of substances and/or fluid properties. For example, the MFC system, without in any way limiting its scope, can be used for determining asphaltenes, saturates, resins, aromatics, solid particulate content, hydrocarbon composition and content, gas composition $C_1$-$C_6$ and content, $CO_2$, $H_2S$ a gas component of a gas phase of the petroleum, total stream percentage of water, gas, oil, solid particles, solid types, oil finger printing, reservoir continuity, oil type, and water elements including ion composition and content, anions, cations, salinity, organics, pH, mixing ratios, tracer components, contamination, or other hydrocarbon, gas, solids or water property that can be related to spectral characteristics using molecular factor methods.

An MFC system can be used to quickly and more efficiently analyze a reservoir fluid, for example at the well site or downhole. The spectral detectivity and sensitivity of the spectroscopy system can be enhanced with the use of a thermal MFC detector and/or one or more MFC filters. An MFC detector can contain one or more layers that are made from the fluid's property of interest (e.g., resins or $CO_2$) or a substance that has the same or very similar absorption and reflectance peaks as the fluid's property of interest. The filter(s) of the MFC system can also be made from the fluid's property of interest (e.g., resins or $CO_2$) or a substance that has the same or very similar absorption and reflectance peaks as the fluid's property of interest. In this manner, the system can be fine-tuned to detect and quantify the property or properties of interest in the reservoir fluid.

According to an embodiment, a method of analyzing a reservoir fluid comprises: providing an analyzer, wherein the analyzer is a molecular factor computational (MFC) system; and determining at least one property of the reservoir fluid using the analyzer, wherein the step of determining comprises: causing or allowing energy to interact with the reservoir fluid; and detecting the interaction between the energy and the reservoir fluid.

Any discussion of the embodiments regarding the analysis of the reservoir fluid is intended to apply to all of the method embodiments. Any discussion of a particular component of an embodiment (e.g., a filter) is meant to include the singular form of the component and also the plural form of the component, without the need to continually refer to the component in both the singular and plural form throughout. For example, if a discussion involves "the filter 118," it is to be understood that the discussion pertains to one filter (singular) and two or more filters (plural).

Turning to the Figures, FIG. 1 is a block diagram of the analyzer according to an embodiment. The analyzer is a molecular factor computational "MFC" system 100. The MFC system 100 includes an energy source 102. The energy source can be a light source 102, for example, a broad-spectrum source; that is, the spectrum is at least substantially continuous. According to an embodiment, the light source 102 includes a tungsten filament. The energy source can also be a heat source, for example, from a hot plate or other heat-generating device. Although reference to a light source may be discussed regarding the energy source, it is to be understood that any energy source can also be used instead of a light source. The light source 102 can be either a tunable laser or a laser emitting an at least substantially continuous spectrum between upper and lower wavelength limits. According to another embodiment, the light source 102 includes a broad-spectrum source and a band-gap filter, which is an optical filter that selects certain spectra for passage and rejects others. A non-continuous spectrum light source can also be used, for example, so long as there is suitable overlap between the absorption spectrum of the molecular absorption filter(s) and/or molecular absorption layers of the detector and the light provided from the light source 102. A power source (not shown) can supply power to the light source 102.

Light from the light source 102 is then passed through the reservoir fluid 104, which interacts with the light as a function of the reservoir fluid's 104 reflection, absorption, transmission, or diffraction.

The wavelengths of light that the reservoir fluid 104 absorbs from the light source 102 produce an absorption spectrum. In an absorption spectrum, portions of a continuous spectrum (light containing all wavelengths) are missing because they have been absorbed by the reservoir fluid through which the light has passed; the missing wavelengths appear as dark lines or gaps when viewing the absorption spectrum. This is contrasted with an emission spectrum, which consists of all the radiations emitted by atoms or molecules of an incandescent material. The missing portions of an absorption spectrum provide information as to the make-up of the reservoir fluid 104 because the missing portions correspond to the constituents of the specimen 104 that absorb the missing wavelengths.

The MFC system 100 also includes a detector 120. The detector 120 can detect the transmitted wavelengths from the reservoir fluid 104 or the reflected wavelengths from the reservoir fluid. There can also be more than one detector 120 making up the MFC system 100, wherein the detectors can be the same or different (e.g., both transmittance detectors or one transmittance and one reflectance detector). The MFC system 100 also includes a processor 122. The detector 120 sends the spectral information to the processor 122. The processor 122 is any computer or device that stores information and executes software or performs a command.

Figure 2:
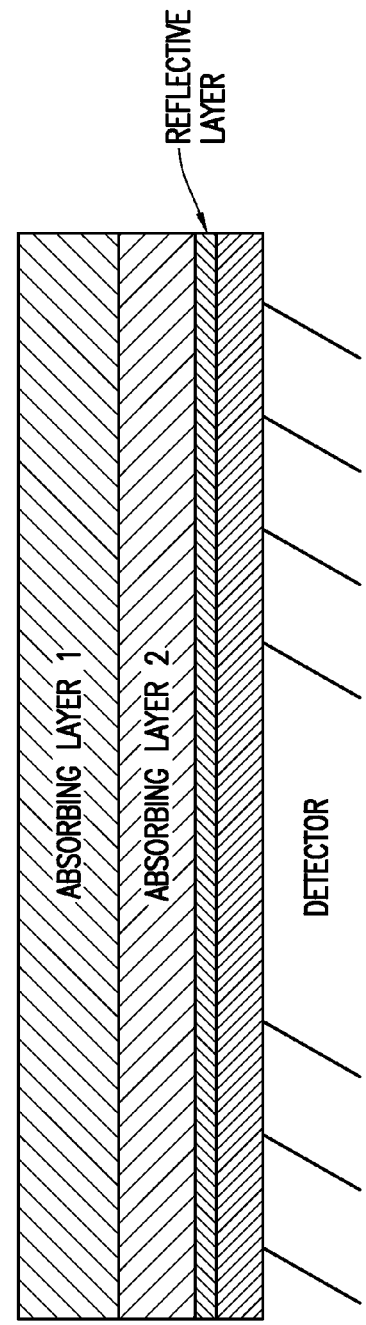
FIG. 2 is a schematic illustration of a molecular factor computational detector according to an embodiment.

According to an embodiment, the detector 120 is a molecular factor computational "MFC" detector. The MFC detector can be a thermal detector. FIGS. 2 and 3 illustrate an MFC detector 120 according to certain embodiments. The MFC detector 120 can include at least one absorbing layer and a reflective layer. The reflective layer is used to ensure that the detector only responds to the wavelengths of interest (i.e., those that are absorbed by the property of interest). Accordingly, any suitable wavelengths from the light source 102 can be used including, but not limited to, ultraviolet "UV," microwave, infrared "IR," etc. Preferably, the wavelength used is in the IR range. Accordingly, the reflective layer can be made from any material that is highly reflective in the infrared range, including but not limited to gold, silver, or aluminum. Other suitable reflective materials can be used depending on the wavelength of interest. For instance, other mirror materials, such as interference coatings or the like can be used.

An absorbing layer is applied to the metallic surface, which gives rise to a thermal detector with a response that is similar to the absorption spectrum of the property of interest, which allows the MFC detector 120 to be 'tuned' to a specific spectral region of interest. As an MFC detector 120, the absorbing layer can be made from the exact property of interest. By way of example, if the property of interest is resins, then the absorbing layer can be made from resins. For gases, such as $CO_2$, the absorbing layer can be the gas contained within a glass or other non-absorbing or non-interfering container. If it is not possible to create the absorbing layer with the exact property of interest, then the absorbing layer can be made from a substance that exhibits an absorption spectrum the same as or very similar to the property of interest. For example, if the analyte of interest is an oil type that contains an ester, the absorbing layer could be any material that contains an ester and has good thin film properties. Accordingly, the MFC detector 120 is most sensitive at the absorbed wavelengths and insensitive to other wavelengths. Another variation of this method is to apply a second absorbing layer in addition to the first absorbing layer. The further absorbing layer(s) would then act as additional filters that could be "activated" by adjusting the chopping frequency of the light source 102. It is to be understood that the absorbing layers can be used with the transmittance detector and/or a reflectance detector.

Each of the absorbing layers of the MFC detector 120 can be designed to determine and quantify one or more properties of interest from the reservoir fluid 104. According to another embodiment, a first layer can be used to determine and quantify only one property of interest while a second layer can be used to determine and quantify another property of interest. In this manner, there can be multiple properties of the reservoir fluid 104 that can be determined and quantified. Each layer can also determine and quantify more than one property of interest of the reservoir fluid.

As can be seen in FIG. 3, the thermal thickness of each of the absorbing layers can be modified such that the layer of interest is responsive to the interacted light. The light source 102 can have a frequency (f) modulation that creates a thermal wave within the layers due to the absorption of light. This thermal wave is detected and the response is dependent upon the amount of light absorbed by the layer. The thermal diffusion length (Ts) is the depth at which the thermal wave's amplitude has been attenuated by a factor of 1/e and is defined by the equation, $$Ts = \frac{1}{a} = \sqrt{\frac{\alpha_s}{\pi f}} \qquad \text{Eq. 1}$$

where a is the thermal diffusivity (m²/s) of the layer. At a given wavelength, the thermal thickness $(T_s)$ is dependent on the frequency modulation f (Hz) of the light. Therefore, by varying the modulation frequency, the detecting depth is controlled. This allows for the development of an MFC detector 120 with two (or more) absorbing layers deposited onto the detector. A modulation frequency could be found that would allow all layers to be thermally thin, which would allow the detection of thermal waves due to the absorption in all layers, as shown in FIG. 3*b*. This would give a detector response related to the absorbances within each layer combined. However, if the light is modulated at a higher frequency, then the bottom layer(s) could remain thermally thin while the top layer(s) is outside of $T_s$ and the detector response would correspond only to the absorption within the bottom layer(s), as shown in FIG. 3*c*. This would result in the top layer(s) essentially acting as a filter, which would lead to a similar response as if those top layers formed a separate filter system in front of the detector. Of course, the frequency can be modulated any number of times both at a higher and lower frequency such that the desired layer is responsive to the interacted light; and therefore, the desired property of interest can be determined using the appropriate layer.

The methods include the step of determining at least one property of the reservoir fluid 104 using the MFC system 100 analyzer. The at least one property can be selected from the group consisting of: asphaltenes, saturates, resins, aromatics, solid particulate content, hydrocarbon composition and content, gas composition $C_1$-$C_6$ and content, $CO_2$, $H_2S$ a petroleum formation factor, viscosity, a gas component of a gas phase of the petroleum, total stream percentage of water, gas, oil, solid particles, solid types, oil finger printing, reservoir continuity, oil type, and water elements including ion composition and content, anions, cations, salinity, organics, pH, mixing ratios, tracer components, contamination, or other hydrocarbon, gas, solids or water property that can be related to spectral characteristics using molecular factor methods.

It may be desirable to determine more than one property of the reservoir fluid 104. The methods can further include the step of determining two or more properties of the reservoir fluid 104 using the MFC system 100. According to this embodiment, the MFC detector 120 can include more than one absorbing layer for determining one or more properties of the reservoir fluid 104 per layer. The MFC system 100 can also include more than one detector 120, for example, as illustrated in FIG. 5, wherein each detector can determine at least one property of the reservoir fluid 104.

Figure 5:
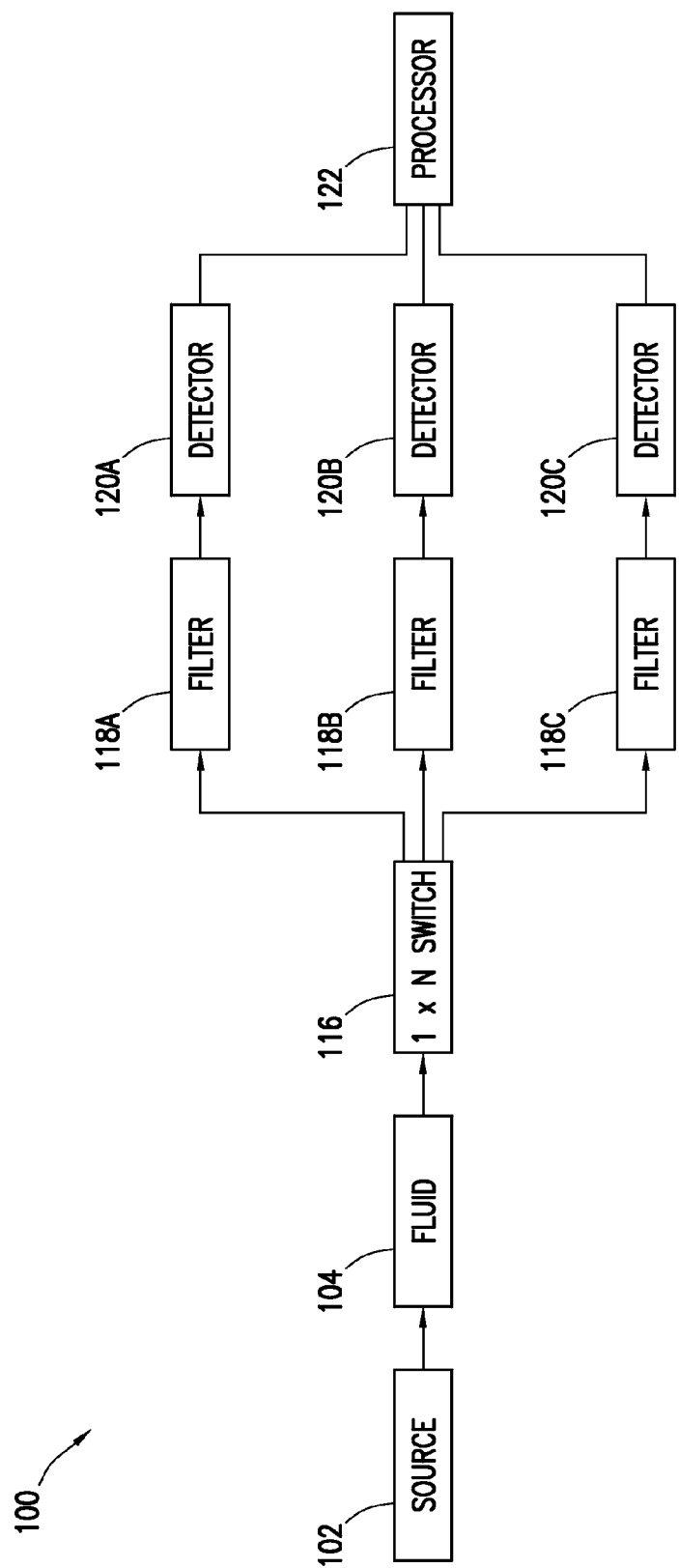
FIG. 5 is a block diagram of an MFC system utilizing multiple filters and detectors and a switch according to another embodiment.

As can be seen in FIGS. 4 and 5, the MFC system 100 can further comprise a filter 118. According to an embodiment, if the detector 120 is an MFC detector, then the filter is a band-gap filter. According to another embodiment, if the detector 120 is not an MFC detector, then the filter 118 is a molecular factor computational "MFC" filter. The MFC filter can be made from the exact substance as the property of interest or a substance that has a very similar absorption spectrum. As can be seen in FIG. 4, the filter 118 can be placed between the reservoir fluid 104 and the detector 120. In this manner, the filter 118 selects which wavelengths reach the detector 120. Placing an MFC filter 118 in the light path containing an absorption spectrum from the reservoir fluid 104 will have different results depending on whether the property for which the filter is specific is present in the reservoir fluid. If the property producing the absorption spectrum of the MFC filter 118 is contained in the reservoir fluid 104, then there will not be a reduction of the light passing through the filter 118. The MFC filter 118 does not reduce the light intensity because the reservoir fluid 104 has absorbed all those wavelengths. However, if the property producing the absorption spectrum of the MFC filter 118 is not contained in the reservoir fluid 104, then there will be a reduction of the light passing through the MFC filter 118. The reduction in the intensity of light passing through both the reservoir fluid 104 and the MFC filter 118 is due to the filter 118 absorbing wavelengths passed by the reservoir fluid 104. According to this embodiment, the detector 120 is responsive to the wavelengths of interest; that is, the detector 120 is sensitive to the light intensity over a wavelength range that encompasses the absorption spectra containing the information used to determine the properties of the reservoir fluid 104. In this manner, one or more properties of the reservoir fluid can be determined. There can also be more than one filter 118 with each of the filters positioned serially between the reservoir fluid 104 and the detector 120. Each of the filters 118 can be specific for a particular property of interest. In this manner, more than one property of the reservoir fluid can be determined and quantified.

According to an embodiment, the methods further include quantifying the property of interest. The system can be used to quantify the property of interest, if present in the reservoir fluid 104. Accordingly, the light can interact with the reservoir fluid 104 without the MFC filter 118 in place, and the intensity of the light at one or more wavelengths of interest can be measured by the detector 120. The light can then interact with the reservoir fluid 104 again with the MFC filter 118 in place. The detector 120 can then measure any difference in the intensity of light. This difference can be used to quantify the property of interest.

Turning to FIG. 5, the MFC system 100 can include a 1×N switch 116 and multiple filters 118, MFC filters 118, detectors 120, MFC detectors 120, and combinations thereof. The light from the light source 102 passes through the reservoir fluid 104. The resulting light beam, which is the transmission spectrum of the reservoir fluid 104, passes through the 1×N switch 116 that directs the light beam through one of several pairs of filters 118 and detectors 120. By operating the switch 116 to select each of the filters 118A, 118B, 118C sequentially in rapid succession, the reservoir fluid 104 is quickly screened for containing one of the properties of interest represented by the MFC filter 118. If the reservoir fluid 104 is a flowing or moving fluid, then this embodiment allows for real-time monitoring and screening of the reservoir fluid 104 for specific properties of interest. Although the 1×N switch 116 is shown in the drawings as a 1×3 switch, those skilled in the art will recognize that the number of ports (N) on the switch 116 must be at least as great as the number of filters 118 desired to be used.

According to an embodiment, one of the filters 118A is a neutral density filter or other reference filter that passes the complete spectrum. The output of the neutral density filter 118A provides a reference or base line to compare to the output of the other filters 118B and/or 118C. In this manner, determination of the property and quantification can occur very efficiently and quickly.

It is to be understood that numerous combinations of filters, MFC filters, detectors, and MFC detectors can be used according to the disclosure. One of ordinary skill in the art, with the benefit of this disclosure, will be able to select the appropriate combination of components of the MFC system depending on the properties of interest to be analyzed.

The reservoir fluid 104 that is analyzed can either be a static fluid or a moving fluid, such as a fluid stream. The reservoir fluid 104 can also be a sample. The step of determining can be performed underground within a wellbore or subterranean formation or it can be performed above ground. The MFC system 100 can also be used under the water for off-shore drilling.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is, therefore, evident that the particular illustrative embodiments disclosed above may be altered or modified and all such variations are considered within the scope and spirit of the present invention. While compositions and methods are described in terms of "comprising," "containing," or "including" various components or steps, the compositions and methods also can "consist essentially of" or "consist of" the various components and steps. Whenever a numerical range with a lower limit and an upper limit is disclosed, any number and any included range falling within the range is specifically disclosed. In particular, every range of values (of the form, "from about a to about b," or, equivalently, "from approximately a to b,") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

What is claimed is:

1. A method of analyzing a reservoir fluid in real-time comprising:
    providing an analyzer, wherein the analyzer is a molecular factor computational system;
    wherein the molecular factor computational system comprises a processor, an energy source, and at least two pairs of a detector and a filter; and
    determining at least one property of the reservoir fluid using the analyzer, wherein the step of determining comprises:
        causing or allowing energy from the energy source to interact with the reservoir fluid as the reservoir fluid is flowing;
        detecting the interaction between the energy and the reservoir fluid as it is flowing; and
        screening the reservoir fluid for the at least one property in real-time as it is flowing;
    wherein the molecular factor computational system further comprises a switch that directs the energy source through the at least two pairs of a detector and a filter, and wherein the method further comprises operating the switch to select the individual filters in succession to screen for at least two properties in real-time; wherein at least one pair of a detector and a filter comprises a non-molecular factor computational detector and a molecular factor computational filter, and wherein at least one pair of a detector and a filter comprises a molecular factor computational thermal detector and a non-molecular factor computational filter; wherein the molecular factor computational thermal detector comprises at least one absorbing layer and a reflective layer.

2. The method according to claim 1, wherein the energy source is a light source.

3. The method according to claim 1, wherein the detector sends spectral information about the reservoir fluid to the processor.

4. The method according to claim 1, wherein the absorbing layer is made from the at least one of the same materials of the reservoir fluid, and wherein this material may be determined as the at least one property.

5. The method according to claim 1, wherein the at least one property is selected from the group consisting of: asphaltenes, saturates, resins, aromatics, solid particulate content, hydrocarbon composition and content, gas composition $C_1$-$C_6$ and content, $CO_2$, $H_2S$ a petroleum formation factor, viscosity, a gas component of a gas phase of the petroleum, total stream percentage of water, gas, oil, solid particles, solid types, oil finger printing, reservoir continuity, oil type, and water elements including ion composition and content, anions, cations, salinity, organics, pH, mixing ratios, tracer components, contamination, or other hydrocarbon, gas, solids or water property that can be related to spectral characteristics using molecular factor methods.

6. The method according to claim 1, further comprising determining two or more properties of the reservoir fluid using the molecular factor computational system.

7. The method according to claim 6, wherein the molecular factor computational thermal detector determines one or more properties of the reservoir fluid.

8. The method according to claim 6, wherein the molecular factor computational thermal detector comprises two or more absorbing layers, and wherein each of the absorbing layers determines one or more properties of the reservoir fluid.

9. The method according to claim 8, wherein the thermal thickness of each of the absorbing layers can be modified such that the layer of interest is responsive to the interacted light.

10. The method according to claim 1, further comprising quantifying the at least one property of the reservoir fluid.

* * * * *